United States Patent [19]

Ward et al.

[11] Patent Number: 5,041,666

[45] Date of Patent: Aug. 20, 1991

[54] METHOD FOR THE PRODUCTION OF 3,3'4,4'-TETRAAMINOBIPHENYL

[75] Inventors: Bennett C. Ward, Pineville, N.C.; Wilson B. Ray, Beeville; Charles B. Hilton, Corpus Christi, both of Tex.; Anthony J. East, Madison, N.J.; Kenneth G. Davenport, Corpus Christi, Tex.

[73] Assignee: Hoechst Celanese Corporation, Somerville, N.J.

[21] Appl. No.: 82,265

[22] Filed: Aug. 6, 1987

[51] Int. Cl.$^5$ ............................................. C07C 209/32
[52] U.S. Cl. ..................................... 564/309; 564/155; 564/265; 564/319; 564/325
[58] Field of Search ................... 564/265, 309, 155; 568/319, 325

[56] References Cited

U.S. PATENT DOCUMENTS 3,232,890  2/1966  Marvel et al. ................ 564/309 X
4,071,555  1/1978  Zengel et al. ................. 564/265

FOREIGN PATENT DOCUMENTS 170041  11/1983  U.S.S.R. .
487535   2/1984  U.S.S.R. .
667771   3/1952  United Kingdom .............. 564/309

OTHER PUBLICATIONS

Kanakalakshmi et al., J. Ind. Chem. Soc., vol. 46(5) 1969, pp. 444-450.
Kanakalakshmi et al. "Chemical Abstracts", vol. 71, Section No. 49462g (1969).
Olah, "Friedel-Crafts and Related Reactions", vol. I, pp. 201-203.
Adams et al. (Adams), "Organic Reactions", vol. 11, pp. 2-7 and 16-19.
Beckmann, "Berichte", vol. 20, pp. 2580-2585 (1887).

*Primary Examiner*—Richard L. Raymond
*Attorney, Agent, or Firm*—Marvin Turken; Shirley L. Church

[57] ABSTRACT

A method is provided for the production of 3,3', 4,4'-tetraaminobiphenyl (TAB) from biphenyl comprising the following steps:
1) acetylating the biphenyl in the presence of an appropriate Friedel-Crafts catalyst to obtain 4,4'-diacetylbiphenyl (DAcB);
2) oximating the DAcB to form DAcB dioxime;
3) subjecting the dioxime to a double Beckmann rearrangement to obtain N,N-diacetylbenzidine (DiAcBz);
4) nitrating the DiAcBz to obtain 3,3'-dinitro-N,N-diacetylbenzidine (DNAcBz)
5) removing the acetyl groups of the DNAcBz by basic hydrolysis to form 3,3'-dinitrobenzidine (DNB); and
6) reducing the nitrate groups of the DNB to form TAB.

10 Claims, No Drawings

METHOD FOR THE PRODUCTION OF 3,3',4,4'-TETRAAMINOBIPHENYL

BACKGROUND OF THE INVENTION

1. Field of the Invention

This invention relates to a new method for the production of 3,3',4,4'-tetraaminobiphenyl (TAB).

High molecular weight polybenzimidazoles are polymers of high thermal stability and excellent resistance to oxidative or hydrolytic degradation, which can be formed into shaped articles such as fibers, films, and molded articles having very desirable physical properties. As taught by the published literature, these polymers may be prepared, for example, by melt polymerizing an aromatic tetraamine and an aromatic or heterocyclic dicarboxylic acid, ester or anhydride in a one or two stage process; see, for example H. Vogel and C. S. Marvel, Journal of Polymer Science, Vol. L, pages 511–539 (1961); and U.S. Pat. Nos. 26,065; 3,174,946; 3,509,108; 3,551,389; 4,312,976; 3,433,772; and 3,655,632. The most widely used aromatic tetraamine for the production of these polybenzimidazoles is 3,3',4,4'-tetraaminobiphenyl (TAB), while the most commercially significant polybenzimidazole is poly-2,2'-(m-phenylene)-5,5'-bibenzimidazole, which is prepared by polymerizing TAB with a difunctional isophthaloyl compound, such as diphenyl isophthalate or isophthalic acid.

The method for producing TAB hitherto considered to be the most desirable utilizes 3,3'-dichlorobenzidine (DCB) as a starting material. In this method, DCB is subjected to direct ammonolysis with a cuprous chloride catalyst. Variations of this method are shown, for example, in U.S. Pat. Nos. 3,865,876 and 3,943,175.

In another method for producing TAB which has engendered substantial interest, the starting material is benzidine which is acetylated, e.g., with acetic anhydride, to form N,N-diacetylbenzidine. The latter compound is then nitrated with concentrated nitric acid to form 3,3'-dinitro-N,N-diacetylbenzidine which is base hydrolyzed to form 3,3'-dinitrobenzidine. This is then reduced by any of various means to form TAB. An example of this method is disclosed by H. Vogel and C.S. Marvel, J. Poly. Sci., Part Al, 1531 (1963).

Both of the foregoing methods have the disadvantages that they utilize starting materials, viz. DCB and benzidine, which are known carcinogens. This makes such methods relatively expensive and difficult to carry out. Thus, any method for producing TAB utilizing a raw material which is both safer and easier to handle, and is substantially less expensive than DCB and benzidine, would be very desirable.

ADDITIONAL BACKGROUND ART

In addition to the references cited and described previously, the following references are of interest.

U.S.S.R. Patent No. 487535, Feb. 7, 1984, from Otkrytiya, Izobret., Prom. Obraztsy, Tovarnye Znaki, 1984, (5) 240-1 (C.A. 101 (5): 38218u, Derwent Accession No. 84-162908/26) teaches the preparation of 4,4'-diacetylbiphenyl by the acetylation of biphenyl with acetic anhydride in dichloroethane at 15°-25° C., using aluminum chloride as catalyst, with subsequent decomposition of the catalytic complex with a dilute inorganic acid.

U.S.S.R. Patent No. 170,041 (Derwent WPI Accession No. 66-19066F/00 and XRAM Accession No. C66-F19066) teaches the synthesis of 4,4'-diacetyldiphenyl by acetylating diphenyl with acetyl chloride using aluminum chloride as catalyst.

Ganboa et al, Synthetic Communications 13, 941–944 (1983) show the production of certain acyl amines, e.g., benzanilide, by refluxing a solution of an aromatic ketone and hydroxylamine hydrochloride in formic acid.

SUMMARY OF THE INVENTION

In accordance with this invention, a method for producing TAB is provided utilizing as a raw material biphenyl which is much safer to handle and use than DCB or benzidine and is relatively inexpensive compared to the latter compounds. The method comprises the following critical steps: 1) biphenyl is acetylated in the presence of an appropriate Friedel-Crafts catalyst to obtain 4,4'-diacetylbiphenyl (DAcB); 2) 4,4'-diacetylbiphenyl is oximated, e.g., with hydroxylamine or a hydroxylamine salt to obtain the dioxime; 3) the dioxime is subjected to a double Beckmann rearrangement to obtain N,N-diacetylbenzidine (DiAcBz); 4) the N,N-diacetylbenzidine is nitrated to obtain 3,3'-dinitro-N,N-diacetylbenzidine (DNAcBz); 5) the acetyl groups of the 3,3'-dinitro-N,N-diacetylbenzidine are removed by basic hydrolysis to form 3,3'-dinitrobenzidine (DNB); and 6) the nitrate groups of the 3,3'-dinitrobenzidine are reduced to form TAB. In some instances it is possible to combine steps 2) and 3), i.e., the dioximation and double Beckmann rearrangement, in a single reaction, as will be more fully discussed hereinafter.

The Friedel-Crafts acetylation of biphenyl to produce 4,4'-diacetylbiphenyl (DAcB) proceeds in accordance with equation (I):

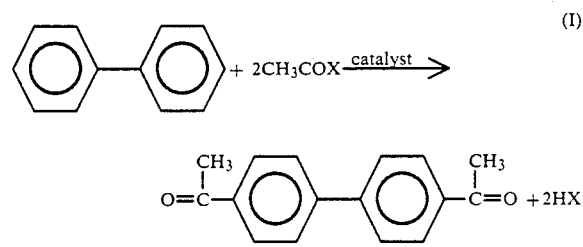

where X is the residue minus an acetyl group of compounds which are known acetylating agents. X may be, for example, hydroxy, acetoxy, or halide including fluoride, chloride, or bromide.

The oximation of the DAcB to form its dioxime proceeds as in equation (II):

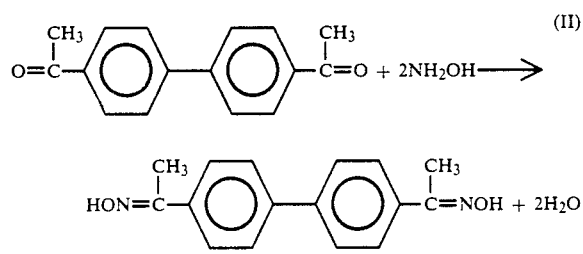

The double Beckmann rearrangement of the dioxime to form the N,N-diacetylbenzidine (DiAcBz) proceeds as in equation (III):

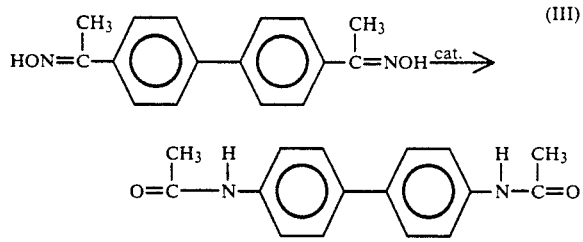

If the oximation and Beckmann rearrangement are carried out in a single step, the reaction proceeds as in equation (IV):

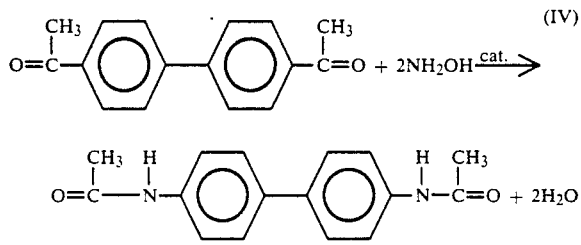

The nitration of DiAcBz to form 3,3′-dinitro-N,N-diacetybenzidine (DNAcBz) proceeds as in equation (V):

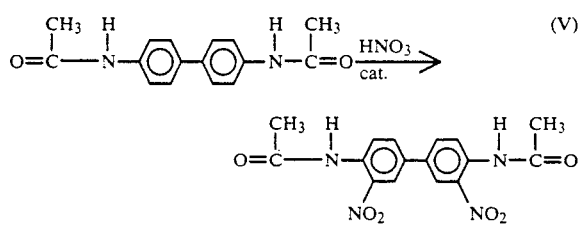

The basic hydrolysis of DNAcBz to form 3,3′-dinitrobenzidine (DNB) proceeds as in equation (VI):

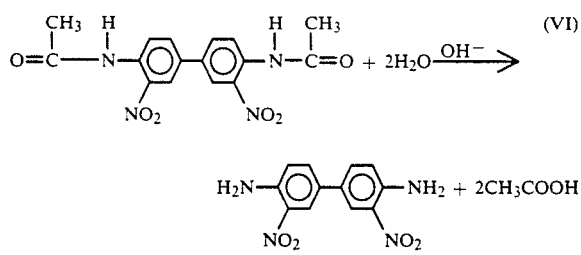

The reduction of DNB to form TAB proceeds in accordance with equation (VII) were "[H]" represents the available hydrogen in hydrogen gas added as is or liberated in situ., e.g., by reacting a metal such as iron with a strong acid such as Hcl, in the presence of a hydrogenation catalyst, or the available hydrogen in a hydrogen-containing reducing agent such as hydrazine, sodium borohydride, or lithium aluminum hydride:

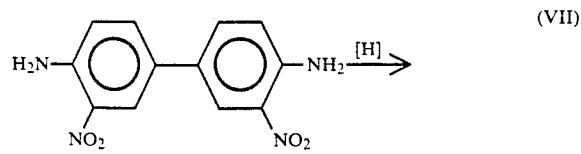

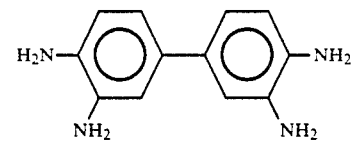

The acetylation of biphenyl shown in equation (I) is accomplished in the presence of an effective Friedel-Crafts catalyst which may be for example, a combination of hydrogen fluoride and boron trifluoroide, an aluminum halide such as aluminum chloride, or any other Friedel-Crafts catalyst which is effective for the reaction, e.g., a halide of beryllium (+3 or +5), cadmium, zinc, gallium, titanium, zirconium, tin, antimony, bismuth or iron (+3); a combination of hydrogen fluoride and antimony pentafluoride; or trifluoromethanesulfonic acid.

The reaction is carried out at an appropriate temperature for each system. Acetylating agents which may be used are, for example, acetic acid, acetic anhydride, acetyl fluoride, acetyl chloride, acetyl bromide, methyl acetate or ketene, which results from the abstraction of HX from the foregoing acetylating agents prior to the acetylation reaction. The acetylating agent other than acetic anhydride may be used in an amount, for example, of about 2 to 8 moles, preferably about 2.2 to 4.0 moles per mole of biphenyl employed. If acetic anhydride is the acetylating agent, it may be used in an amount of about 1 to 4 moles, preferably about 1.1 to 2.0 moles, per mole of biphenyl. In carrying out the reaction, biphenyl, acetylating agent, and catalyst, may be charged to a corrosion-resistant reactor and the mixture maintained at a temperature appropriate for the system employed. In many cases, the temperature will be in the range, for example, of about $-78°$ to $125°$ C. With systems utilizing a combination of HF and $BF_3$ as catalyst, the temperature of reaction will generally not be above about $72°$ C. The time of reaction may be in the range, for example, of about 1.0 to about 24 hours. The pressure is uncritical and atmospheric or autogenous pressure may be utilized. If HF is used as a catalytic component, it may be charged as a liquid or a gas using technologies of handling well-known to those skilled in the art. In many systems, an inert gas such as nitrogen may be used to keep sufficient gaseous catalytic components, e.g., HF and $BF_3$, in contact with the reacting mixture. The catalyst or catalyst component other than HF may be present, for example in the range of about 2 to 6 moles preferably about 3 to 4 moles per mole of biphenyl initially added to the reaction zone. If a combination of HF and $BF_3$ or $SbF_5$ is the catalyst, the HF may be present in an amount, for example, of about 10 to 100 moles, preferably about 25 to 75 moles per mole of biphenyl initially present in the reaction zone.

The formation of the dioxime of 4,4′-diacetylbiphenyl (DAcB) in accordance with equation (II) is accomplished, for example, by contacting the DAcB with hydroxylamine or a salt of hydroxylamine, e.g., hydroxylamine hydrochloride, hydroxylamine sulfate, hydroxylamine bisulfate, or hydroxylamine phosphate, and, optionally, a base, such as ammonium hydroxide, potassium hydroxide, sodium hydroxide or lithium hydroxide, at a temperature, for example of about $20°$ to $120°$ C. for a period, for example, of about 1 to 4 hours. Any pressure may be used, e.g., about 80 mm. of mercury to 10 atmospheres absolute. The reaction may be carried out, for example, in an aqueous or alcoholic medium, i.e., in the presence of water and/or an alcohol such as methanol, ethanol, or isopropanol, or an aqueous solution of a water-soluble carboxylic acid, e.g., an alkanoic acid such as acetic.

The DAcB dioxime is converted into N,N-diacetylbenzidine (DiAcBz) by a Beckmann rearrangement as shown in equation (III), by contacting the dioxime with a catalyst for the reaction at a temperature, for example, of about 0° to 118° C. for a period for example of about 0.25 to 4 hours. The pressure is not critical and may be, for example, in the range of about 80 mm. of mercury to 10 atmospheres absolute. Any Beckmann rearrangement catalyst may be used as, for example, an acid, e.g., a mineral acid such as sulfuric or hydrochloric acid, an organic acid such as trifluoroacetic acid, para-toluenesulfonic acid, benzenesulfonic acid, or methanesulfonic acid, an acidic ion-exchange resin such as Amberlyst 15 or Nafion 501 which are sulfonic acid ion-exchange resins, thionyl chloride, or phosphoryl chloride. The reaction may be advantageously carried out in the presence of a solvent such as nitroethane, ethyl acetate, or mixtures of ethyl acetate and tetrahydrofuran. The total amount of solvent is not critical but is usually present such that the oxime concentration is in the range of about 2 to 50 percent by weight at the start of the reaction.

If it is desired to combine the dioximation and double Beckmann rearranqement in one reaction, the conditions described previously for oximation may be used except that the solvent/catalyst employed is an anhydrous acidic solvent such as formic, acetic, or methanesulfonic acid in the absence of a base. In carrying out the combined reaction, the temperature employed may be, for example, in the range of about 75° C. to refluxing temperature, preferably about 90° C. to refluxing temperature.

The nitration of the DiAcBz to produce 3,3'-dinitro-N,N-diacetylbenzidine (DNAcBz) is accomplished by methods well known in the art for the nitration of aromatic compounds. For example, the DiAcBz may be contacted with a nitric acid solution containing about 5 to 15 wt. % $HNO_3$ at a low temperature, e.g., about $-10°$ to 20° C. for about 10 to 120 min. A specific procedure of this type utilizing 90% fuming nitric acid is described in the second Vogel and Marvel article cited previously. Alternatively, the DiAcBz may be contacted with a mixture of nitric acid, glacial acetic acid and acetic anhydride, containing, for example, about 20 to 50 wt. % of nitric acid at a temperature, for example, of about $-10$ to period, for example of about 10 to 120 min. Still another procedure is to contact the DiAcBz with a mixture of nitric acid and sulfuric acid containing, for example about 5 to 25 wt. % of nitric acid at a temperature, for example of about 0° to 120° C., for a period, for example, of about 10 to 120 min.

The basic hydrolysis of the DNAcBz to form 3,3'-dinitrobenzidine (DNB) as shown in equation (VI) is accomplished, for example, by heating the DNAcBz, e.g., at a temperature of about 25° C. to refluxing temperature, with a solution of about 10 to 50 wt. % of a base, e.g., potassium or sodium hydroxide, or an alkyl amine, in water or an aqueous alcohol, e.g. ethanol, methanol, or t-butanol, containing about 10 to 50 wt. % of the alcohol, for a period, for example, of about 1 to 24 hours.

The reduction of DNB to produce TAB as shown in equation (VII) may be accomplished, for example, by contacting DNB as is or dissolved in an appropriate solvent with a hydrogenation catalyst in the presence of hydrogen. The solvent may be, for example, methanol, ethanol, t-butanol, aqueous alcohol, toluene, diethyl ether, tetrahydrofuran, or 1,4 dioxane, and the DNB:solvent weight ratio may be in the range, for example of about 1:1 to 1:100, preferably about 1:2 to 1:20. The hydrogenation catalyst may be, for example, a transition metal on a suitable support. Preferred transition metals are the noble metals, e.g., palladium, ruthenium, platinum, rhodium, iridium, and osmium, and some suitable supports are, for example, carbon, alumina, silica, and polymeric resins. The metal concentration on the support in weight ratio of metal:support may be in the range, for example, of about 1:100 to 1:2, preferably about 1:50 to 1:10, and the weight ratio of catalyst system:DNB is, for example, in the range of about 1:500 to 1:2, preferably about 1:30 to 1:5. In carrying out the reaction, the hydrogen pressure may be in the range, for example, of about 10 to 1200 psig, preferably about 75 to 300 psig; the reaction temperature may be in the range, for example, of about 10° to 150° C., preferably about 20° to 80° C.; and the reaction time may be in the range, for example, of about 0.25 to 10.0 hours, preferably about 1.0 to 4.0 hours.

Alternative to the hydrogenation reaction as described, the reduction reaction shown in equation (III) may be accomplished, for example, by slowly adding to a cooled solution of DNB in a solvent, e.g., an alcohol such as methanol, ethanol, or t-butanol, a glycol such as ethylene glycol, or an ether such as tetrahydrofuran, diethyl ether, or dimethoxyethane, a reducing agent containing available hydrogen, e.g., hydrazine, sodium or potassium borohydride or lithium aluminum hydride, and, if desired, one of the foregoing hydrogenation catalysts, e.g., 5% ruthenium on carbon. The solution may then be warmed to room temperature and heated, e.g., at a temperature of about 0° to 50° C. for a period of about 1 to 4 hours.

Still another procedure which may be used in accomplishing the reduction of DNB to TAB is to contact the DNB with a Bronsted acid, i.e., a proton donor, such as a mineral acid, e.g. HCl, and a appropriate reducing agent, e.g., a free metal capable of being oxidized to metallic ions, e.g., iron, zinc in pure or amalgamated form, and tin, or metallic ions capable of further oxidation, e.g., $Fe^{+2}$ or $Sn^{+2}$. The reaction may be carried out, for example, by slowly adding DNB to a composition combining the Bronsted acid, e.g. concentrated HCl, and the metal or metal ion reducing agent while maintaining the temperature between, for example, about 15° and 60° C. A procedure of this type is described in the second Vogel and Marvel article cited previously.

DESCRIPTION OF SPECIFIC EMBODIMENTS

Example 1

This example illustrates the preparation of 4,4'-diacetylbiphenyl (DiAcB) by the low temperature Friedel-Crafts acetylation of biphenyl as shown in equation (I), using acetyl chloride as acetylating agent and aluminum chloride as catalyst.

A 100 mL 4-necked flask was fitted with a glass paddle stirrer, reflux condenser, tap-funnel and a low temperature thermometer. The condenser and tap-funnel were fitted with drying tubes, and all glassware was dried at 110° C. for several hours prior to use. The flask was charged with 500 mL dry methylene chloride, 96 g (0.72 mol) fresh aluminum trichloride, and 46.2 g (0.30 mol) biphenyl. Stirring was begun, and the mixture rapidly turned chocolate-brown in color. The flask was then cooled to −60° C.

Acetyl chloride, 56.5 g (0.72 mol) was added slowly from the tap funnel with stirring, keeping the flask at −60° C. during the addition. The mixture rapidly changed to a fluorescent purple color. After the acetyl chloride addition was complete (1 hour), the mixture was allowed to warm slowly to room temperature and was stirred for 18 hours. After this period it was a deep carmine red color.

The contents of the flask were poured with good stirring onto a mixture of 500 mL concentrated HCl and 1 Kg crushed ice. The methylene chloride layer was separated, the aqueous layer extracted with 2×300 mL methylene chloride, and the organic layers combined. The methylene chloride extracts were washed with 3×300 mL 10% w/v sodium carbonate, 3×300 ml distilled water, dried (magnesium sulfate), and the solvent removed to give 60 g (85%) of pale pink solid. To separate the soluble monoacetyl derivative from the less soluble diacetyl derivative, the mixture was extracted (Soxhlet) with 400 ml dry ethanol. All the solid dissolved, but upon cooling, solid crystallized. This material was isolated, and melted at 126°–144° C. Residue from the mother liquor, obtained by evaporation, weighed 9.5 g and melted at 100°–110° C., which was identified as impure monoacetyl compound.

The major component was recrystallized from toluene to yield glittering leaflets of 4,4'-diacetylbiphenyl, 14 g (20%), mp 188°–192° C. Evaporation of the toluene liquors gave 32 g of product mp 109°–111° C. This was recrystallized from toluene to give 23.8 g (40%) of p-acetylbiphenyl, mp 110°–112° C.

EXAMPLE 2

This example illustrates the same reaction as Example 1 using acetic anhydride as acetylating agent and a combination of hydrogen fluoride and boron trifluoride as catalyst.

Biphenyl (7.7 g, 0.05 mol) and acetic anydride (10.2 g, 0.1 mol) were added to a 300 cc Hastelloy C autoclave. The autoclave was sealed and evacuated (150 mm HgA) and the contents were cooled to ca −23° C. Hydrogen fluoride (30.0 g, 1.5 mol) and boron trifluoride (34.0 g, 0.5 mol) were added, sequentially, to the stirred mixture. The mixture was then warmed to room temperature and stirred for 2 h. The hydrogen fluoride and boron trifluoride were then vented at room temperature through a caustic scrubber. The autoclave was then opened and the contents were poured onto ice. The resulting slurry was adjusted to pH=6.5 using a 45% solution of potassium hydroxide. The mixture was extracted with ethyl acetate (100 mL, 3×), the organic fractions were combined and dried over anhydrous magnesium sulfate, filtered, and the ethyl acetate was removed on a rotary evaporator to afford 10.6 g of solid. The reaction proceeded with 96.8% conversion of biphenyl and 10.4% selectivity to 4,4'-diacetylbiphenyl.

EXAMPLE 3 TO 8 AND A TO F

These examples illustrate attempts to carry out the acetylation reaction of equation (I) using a procedure similar to that of Example 2 but varying the amounts of biphenyl (B), acetyl chloride (AcCl) or acetic anhydride (Ac₂O) employed as acetylating agent (AcX), hydrogen fluoride (HF) and boron trifluoride (BF₃) and also varying the temperature (T) and time (t) of reaction. The specific conditions employed and the results obtained in terms of weight of product after work-up (Rec), conversion of biphenyl (% Conv), and yield (% Yld) of 4-acetylbiphenyl (M) and 4,4'-diacetylbiphenyl (D), are shown in Table I, wherein Examples 3 to 8 were carried out within the scope of the invention and comparative examples A to F were performed with at least one parameter outside the scope of the invention.

TABLE I

| Ex. | B (mol) | AcX (mol) | HF (mol) | BF$_3$ (mol) | T (°C.) | t (h) | Rec (gr) | % Conv | % Yld M | D |
|---|---|---|---|---|---|---|---|---|---|---|
| A | 0.10 | AcCl/0.30 | 7.5 | 0 | 25 | 19 | 16.8 | 30 | 10 | 0 |
| B | 0.05 | AcCl/0.15 | 3.75 | 0 | 50 | 1 | 6.2 | 49 | 11 | 0 |
| 3 | 0.05 | AcCl/0.15 | 3.75 | 0.2 | 50 | 1 | 8.2 | 100 | 90 | 10 |
| C | 0.05 | AcCl/0.15 | 0 | 0.5 | 50 | 1 | 10.6 | 69 | 65 | 0 |
| 4 | 0.05 | AcCl/0.15 | 3.75 | 0.2 | 50 | 3 | 10.9 | 100 | 46 | 17 |
| D | 0.05 | AcCl/0.15 | 3.75 | 0.2 | 75 | 1 | 18.0 | 100 | 0 | 0 |
| 5 | 0.05 | AcCl/0.15 | 3.75 | 0.5 | 50 | 1 | 13.1 | 100 | 73 | 24 |
| 6 | 0.05 | AcCl/0.15 | 3.75 | 0.5 | 60 | 1 | 12.9 | 100 | 66 | 25 |
| E | 0.05 | Ac₂O/0.15 | 3.75 | 0 | 50 | 3 | 6.8 | 38 | 23 | 0 |
| F | 0.05 | Ac₂O/0.15 | 3.75 | 0 | 70 | 3 | 8.4 | 87 | 82 | 0 |
| 7 | 0.05 | Ac₂O/0.15 | 3.75 | 0.2 | 70 | 3 | 7.8 | 100 | 80 | 5 |
| 8 | 0.05 | Ac₂O/0.15 | 3.75 | 0.5 | 70 | 3 | 12.6 | 100 | 0 | 40 |

The results of Table I show that no DiAcB is obtained if HF alone (Examples A, B, E and F), or BF₃ alone (Example C), is employed, or if a temperature of reaction above about 72° C. is employed (Example D).

EXAMPLE 9

This example illustrates the dioximation of DiAcB as shown in equation (II) using hydroxylamine sulfate as the oximation agent.

A base solution was prepared by adding water (80 mL) and ethanol (20 mL) to a solution of 30% ammonium hydroxide (4 mL). Hydroxylamine sulfate (3.6 g, 0.022 mol) and 4,4'-diacetylbiphenyl (4.8 g, 0.02 mol) were added to the base solution and the mixture was stirred for 1 h at 86° C. The mixture was cooled to room temperature and extracted with ethyl acetate (3×). The organic fractions were combined and dried over anhydrous magnesium sulfate, filtered, and the ethyl acetate was removed on a rotary evaporator. The reaction proceeded with 50.0% conversion of 4,4'-diacetylbiphenyl and 25% and 37% selectivity to mono- and dioxime, respectively.

EXAMPLES 10 TO 14

These examples illustrate the oximation reaction of equation (II) with the conditions being similar to those of Example 9 except for variations in solvent, temperature, and time as shown in Table II, where the solvents as indicated were binary mixtures of water and ethyl alcohol (EtOH) or acetic acid (HOAc) with the weight ratio of first named to second named component being in the range of 2:1 to 4:1. Table II also shows the results of the examples including the percent conversion of DiAcB (% Conv) and the yield of the total of mono- and dioximes (% Yield).

TABLE II

| Ex. | Solvent | Temp (°C.) | t (hrs) | % Conv | % Yield (M & D) |
|---|---|---|---|---|---|
| 10 | $H_2O$:EtOH | 86 | 2 | 15 | 11 |
| 11 | $H_2O$:EtOH | 86 | 3 | 64 | 64 |
| 12 | HOAc:$H_2O$ | 104 | 2 | 91 | 62 |
| 13 | HOAc:$H_2O$ | 108 | 1 | 78 | 59 |
| 14 | EtOH:$H_2O$ | 80 | 1 | 70 | 40 |

EXAMPLE 15

This example illustrates the synthesis of N,N-diacetylbenzidine (DiAcBz) by the double Beckmann rearrangement of DiAcB dioxime as shown in equation (III) using thionyl chloride as catalyst and nitroethane as solvent.

To a 250 mL 3-necked roundbottomed flask equipped with a thermometer, pressure equalizing addition funnel, and condenser were added nitroethane (105 g) and 4,4'-diacetylbiphenyl dioxime (5.0 g, 0.02 mol). The mixture was heated at reflux (50° C., 80 mm HgA) and thionyl chloride (1.5 g 12.6 mmol) was added dropwise. Upon completion of addition of the thionyl chloride, the mixture was heated at reflux for 30 min. The mixture was filtered and the solid was washed with water and dried in a nitrogen stream to afford 3.1 g of light brown-red crystals. The reaction proceeded with 99% conversion of the dioxime and 62% selectivity to DiAcBz.

EXAMPLES 16 TO 20

These examples illustrate the double Beckmann rearrangement of DiAcB dioxime to form DiAcBz in accordance with equation III, using the procedure of Example 15 except that the solvent was ethyl acetate (EtOAc) or a mixture of EtOAc and tetrahydrofuran (THF) in a 4:1 weight ratio and the quantity of thionyl chloride ($SOCl_2$) was varied. The identity of solvent and quantity of $SOCl_2$ as well as the percent conversion of dioxime (% Conv) and percent yield of DiAcBz (% Yield) are shown in Table III.

TABLE III

| Ex. | Solvent | $SOCl_2$ (g) | % Conv | % Yield |
|---|---|---|---|---|
| 16 | EtOAc:THF | 0.5 | <10 | <10 |
| 17 | EtOAc | 0.5 | <10 | <10 |
| 18 | EtOAc:THF | 1.5 | 64 | 13 |
| 19 | EtOAc | 1.5 | 58 | 12 |
| 20 | EtOAc | 4.5 | 97 | 25 |

EXAMPLES 21 TO 24

These examples illustrate the one step oximation-Beckmann rearrangement of DiAcB to form DiAcBz in accordance with equation (IV).

The procedure of Examples 9 to 14 was followed except that the solvent was anhydrous acetic acid (HOAc) or formic acid (HOFo) and the temperature and time of reaction were varied. The conditions of reaction and results in terms of conversion of DiAcB (% Conv) and percent yield of DiAcBz (% Yield) are shown in Table IV.

TABLE IV

| Ex. | Solvent | Temp (°C.) | t (hrs) | % Conv | % Yield |
|---|---|---|---|---|---|
| 21 | HOAc | 25 | 18 | 5 | 3 |
| 22 | HOAc | 118 | 1 | 100 | 86 |
| 23 | HOAc | 118 | 1 | 100 | 96 |
| 24 | HOFo | 104 | 3 | <100 | 61 |

The results of these examples show that the conversion and yield decrease appreciably when temperatures of reaction below about 75° C. are employed.

EXAMPLE 25

This example illustrates the nitration of DiAcBz to form 3,3'-dinitro-N,N-diacetylbenzidine (DNAcBz) in accordance with equation (V).

A nitrating solution is prepared by mixing nitric acid (23.0 g), urea (1 g), and glacial acetic acid (23.0 g) at elevated temperature and allowing the solution to cool. To the solution is slowly added a mixture of DiAcBz (22.5 g, 0.09 mol) in acetic anhydride (34.0 g) and glacial acetic acid (22.0 g). The mixture is stirred for 24 h at room temperature at which time ice is added to precipitate the product. The precipitate is filtered, washed with water, and dried in vacuo to afford DNAcBz.

EXAMPLE 26

This example illustrates the basic hydrolysis of DNAcBz to form 3,3'-dinitrobenzidine (DNB), as shown in equation (VI).

A base solution is prepared by adding a solution of 45% potassium hydroxide to water and ethanol (1:4:1). To the base solution is added DiNAcBz and the resulting mixture is heated at reflux for 1 h. The ethanol is removed in vacuo causing the product to precipitate. the precipitate is filtered, washed with water, and dried in vacuo to afford DNB.

EXAMPLE 27

This example illustrates the formation of 3,3',4,4'-tetraaminobiphenyl (TAB) by the reduction of DNB using gaseous hydrogen and a palladium on carbon hydrogenation catalyst.

To a 300 cc 316 stainless steel autoclave is added DNB (27.4 g, 0.1 mol), methanol (200 mL), and 5% palladium/carbon (5 g). The mixture is stirred (500 rpm) under hydrogen (200 psig) at 50° C. for 2 h. The mixture is filtered and the methanol is removed from the filtrate in vacuo to afford the 3,3',4,4'-tetraaminobiphenyl.

We claim:
1. A method for the production of 3,3',4,4'-tetraaminobiphenyl (TAB) from biphenyl comprising the following steps:
   1) acetylating said biphenyl in the presence of an appropriate Friedel-Crafts catalyst to obtain 4,4'-diacetylbiphenyl (DAcB);
   2) oximating said DAcB to form DAcB dioxime;
   3) subjecting said dioxime to a double Beckmann rearrangement to obtain N,N-diacetylbenzidine (DiAcBz);
   4) nitrating said DiAcBz to obtain 3,3'-dinitro-N,N-diacetylbenzidine (DNAcBz);
   5) removing the acetyl groups of said DNAcBz by basic hydrolysis to form 3,3'-dinitrobenzidine (DNB); and

6) reducing the nitrate groups of said DNB to form TAB.

2. The method of claim 1 wherein said acetylation (step 1) is carried out in the presence of a combination of hydrogen fluoride and boron trifluoride as catalyst and the temperature of reaction is no higher than about 72° C.

3. The method of claim 1 wherein said acetylation (step 1) is carried out in the presence of aluminum chloride as catalyst.

4. The method of claim 1 wherein said oximation (step 2) is carried out by reacting said DAcB with hydroxylamine or a hydroxylamine salt.

5. The method of claim 1 wherein said oximation (step 2) and Beckmann rearrangement (step 3) are combined by reacting said DAcB with hydroxylamine or a hydroxylamine salt in the presence of an anhydrous acidic solvent, and the temperature of reaction is no lower than about 75° C.

6. The method of claim 5 wherein said solvent is anhydrous acetic acid.

7. The method of claim 5 wherein said solvent is anhydrous formic acid.

8. The method of claim 1 wherein said reduction is carried out by reacting said DNB with gaseous hydrogen in the presence of a hydrogenation catalyst.

9. A method for the production of 3,3',4,4'-tetraaminobiphenyl (TAB) from biphenyl comprising the following steps:
　1) acetylating said biphenyl in the presence of either a combination of hydrogen fluoride and boron trifluoride or aluminum chloride as catalyst to obtain 4,4'-diacetylbiphenyl (DAcB);
　2) oximating said DAcB by reacting it with hydroxylamine or a hydroxylamine salt to form DAcB dioxime;
　3) subjecting said dioxime to a double Beckmann rearrangement to obtain N,N-diacetylbenzidine (DiAcBz);
　4) nitrating the DiAcBz to obtain 3,3'-dinitro-N,N-diacetylbenzidine (DNAcBz);
　5) removing the acetyl groups of the DNAcBz by basic hydrolysis to form 3,3'-dinitrobenzidine (DNB); and
　6) reducing the nitrate groups of the DNB by reacting it with gaseous hydrogen in the presence of a hydrogenation catalyst to form TAB.

10. The method of claim 9 wherein said oximation (step 2) and Beckmann rearrangement (step 3) are combined by reacting said DAcB with a hydroxylamine salt in the presence of anhydrous acetic acid or anhydrous formic acid as solvent and the temperature of reaction is no lower than about 75° C.

* * * * *